United States Patent [19]
Fulton

[11] Patent Number: 5,201,321
[45] Date of Patent: Apr. 13, 1993

[54] METHOD AND APPARATUS FOR DIAGNOSING VULNERABILITY TO LETHAL CARDIAC ARRHYTHMIAS

[76] Inventor: Keith W. Fulton, 4655 Wild Indigo #211, Houston, Tex. 77027

[21] Appl. No.: 653,190

[22] Filed: Feb. 11, 1991

[51] Int. Cl.$^5$ ............................................ A61B 5/0472
[52] U.S. Cl. .................................................... 128/702
[58] Field of Search ................................. 128/702-706; 364/413.06

[56] References Cited

U.S. PATENT DOCUMENTS

| | | |
|---|---|---|
| 3,518,983 | 7/1970 | Jorgensen .......................... 128/702 |
| 3,699,949 | 10/1972 | O'Hanlon, Jr. et al. ............ 128/726 |
| 3,755,783 | 8/1973 | Astarjian et al. ................... 128/702 |
| 3,902,479 | 9/1975 | Chaumet ............................. 128/703 |
| 4,411,271 | 10/1983 | Markowitz .......................... 128/703 |
| 4,732,157 | 3/1988 | Kaplan et al. ...................... 128/703 |
| 4,924,875 | 5/1990 | Chamoun ............................ 128/703 |

Primary Examiner—William E. Kamm
Attorney, Agent, or Firm—Gunn, Lee & Miller

[57] ABSTRACT

A method and apparatus for diagnosing the vulnerability of a patient's heart to lethal cardiac arrhythmias uses on-line comparison of the beat timing vectors with the stored vectors of a number of previous beats and analyzing the vector differences according to a chaos techniques to obtain an indication of heart condition.

11 Claims, 12 Drawing Sheets

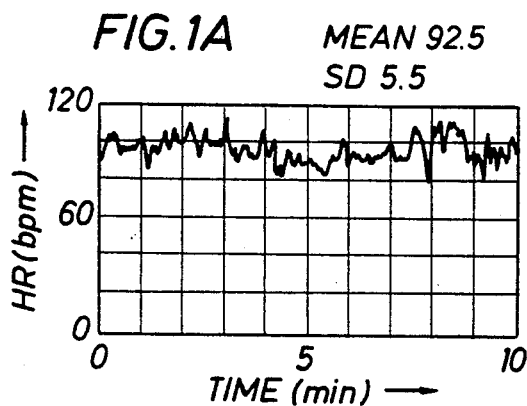
FIG.1A  MEAN 92.5  SD 5.5
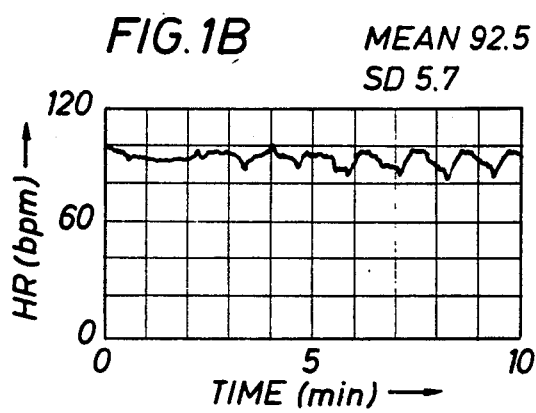
FIG.1B  MEAN 92.5  SD 5.7
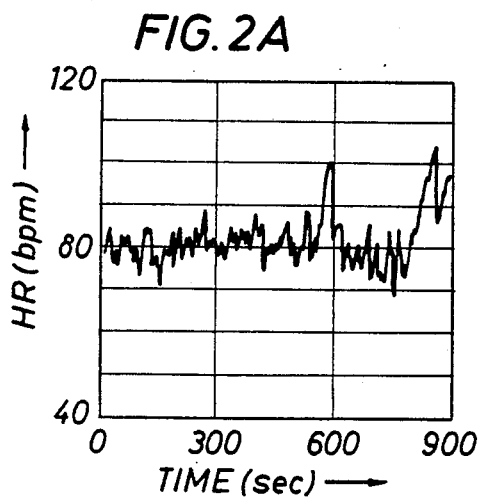
FIG.2A
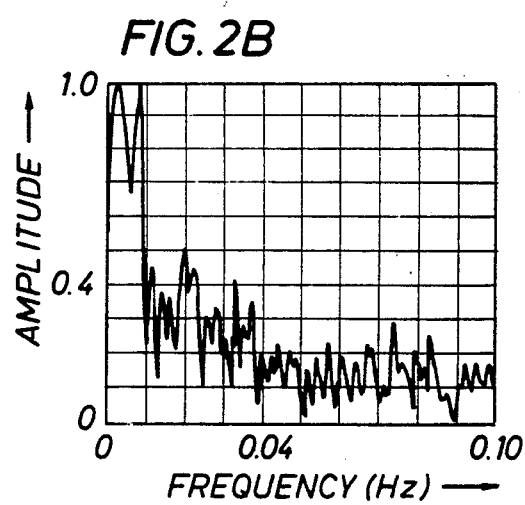
FIG.2B
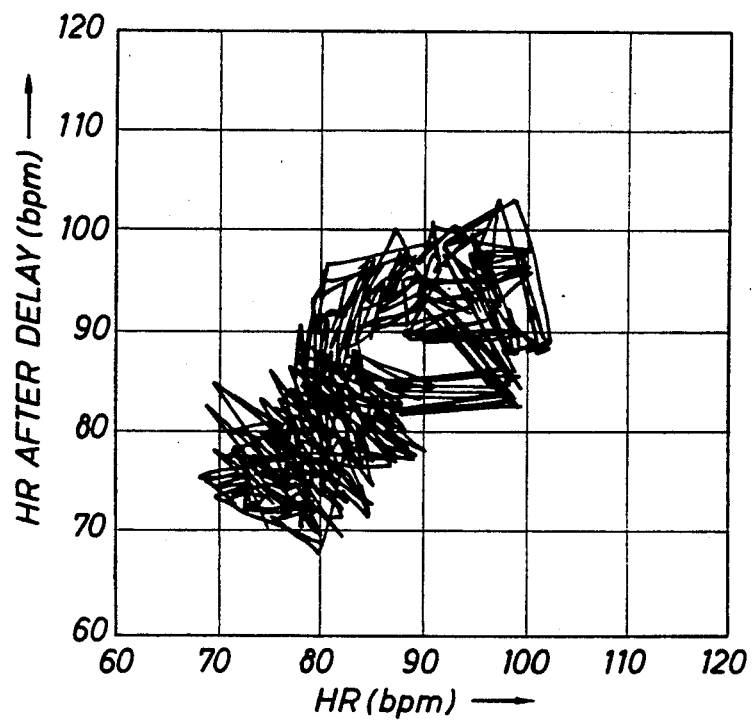
FIG.2C

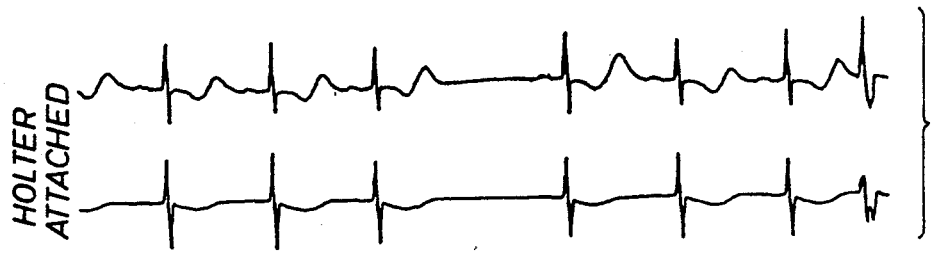
FIG. 13A
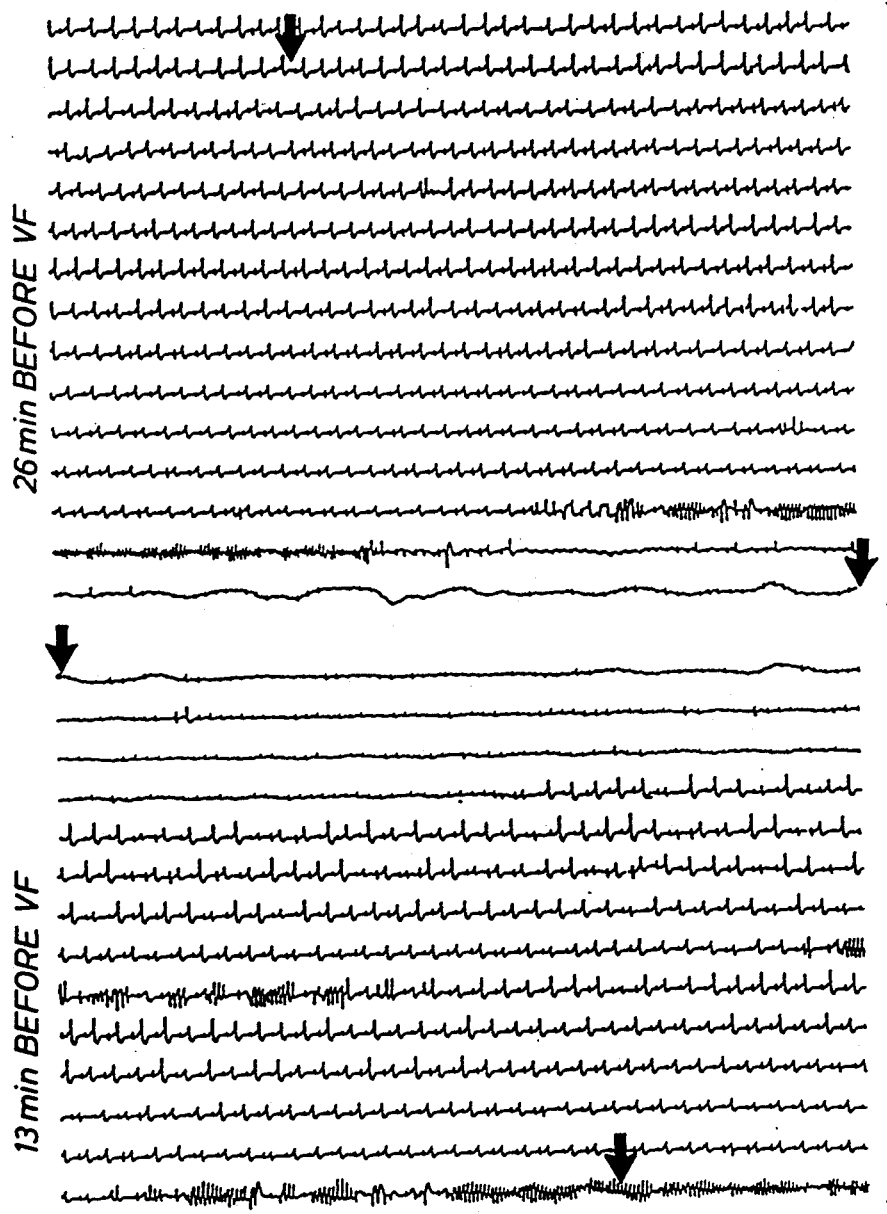
FIG. 13B
FIG. 13C

METHOD AND APPARATUS FOR DIAGNOSING VULNERABILITY TO LETHAL CARDIAC ARRHYTHMIAS

BACKGROUND OF THE DISCLOSURE

In groups of patients with a recent myocardial infarction, several physiological measures of the heartbeat are known to be reasonably good prospective predictors of lethal arrhythmogenesis. Kleiger et al., (1987) showed that the reduced standard deviation of the R-R intervals was a statistically significant predictor. La Rovere et al., (1988) demonstrated that a reduced sensitivity of the R-R interval to high levels of blood pressure (i.e., a reduced baroreflex sensitivity) also was a predictor. It is interesting, however, that although the standard deviation of the R-R intervals and the baroreflex sensitivity are predictors between groups of subjects, when each measure is obtained from the same patient they are not found to be correlated (Bigger et al., 1989). This result could be explained by each being correlated with a third event.

The modulation of the heartbeat is attributed to three neural reflexes which occur during either respiration, low-level blood-pressure regulation, or body temperature change (Kitney, 1987). It has recently been proposed that in the normal heart this net modulation produces a "fractal" series of R-R intervals manifesting nonlinear dynamics that converts to a more regular and linear pattern when the heart becomes vulnerable to lethal arrhythmogenesis (Goldberger et al., 1988). Analysis of the heartbeat intervals with an algorithm for calculating the correlation dimension would be relevant to this hypothesis, because if the correlation dimension was found to be a fraction, it would imply a "fractal" time series. The "pointwise" correlation dimension (Mayer-Kress et al., 1988) has been used to evaluate R-R interval data, but, because of the large error of estimation, it has been impossible to know whether or not the calculated value is a fraction or an integer.

Using the Point-$D_2$ algorithm set forth in this disclosure, to eliminate nonconvergent data points, Skinner, Carpeggiani, Landisman and Fulton (Circulation Research, 1990, submitted) analyzed records from eight conscious pigs before and during myocardial ischemia. They found that coronary artery constriction evokes a reduction in the correlation dimension that drops from 2.50 +/−0.81 during control periods to 1.07+/−0.18 during the minute just before the occurrence of the lethal arrhythmia, ventricular fibrillation.

The same effect has been observed by the researchers in a human patient who died while wearing a heartbeat monitor. That is, many minutes (and hopefully days) before the patient's heart manifested lethal arrhythmia, his heartbeat dimensionality showed excursions to the vicinity of 1.0. During the 13 minutes preceding the lethal arrhythmogenesis, the mean Point-$D_2$ dropped to 1.0 and the standard deviation became markedly reduced.

It is simplistic to measure a specific point (usually R-R) of the heartbeat for a series of N heartbeats (wherein N typically is in the range of perhaps 5000 to 50,000), note the scatter, apply known statistical methods of analysis and thereby measure some precursor aspect of the heartbeat. As will be discussed with regard to one of the attached figures, a healthy heartbeat is shown with a particular heart rate (BPM or beats per minute) with a standard deviation; it is also presented for a heart in a failure mode where both the average heart rate and standard deviation are the same. Variations in heart rate do not express a failure condition solely through statistical analysis.

The present method and apparatus contemplate location of the peak in the heart rate signal obtained by appropriately attached electrodes which provide an output of the heartbeat signal. In the preferred version of the present apparatus, the signal is sampled and digitized to thereby convert from analog to digital values. The sampling rate need not be excessive; the sampling rate can be as low as perhaps 128 samples per second, the preferred rate being about 256 or 512 samples per second. While a greater number of samples can be obtained, there is an increase in precision as the sampling rate increases. The sampling rate can be carried to a desired level of precision. In any event, sampling and digitizing is carried out typically at that rate. For purposes of digitizing, an analog to digital converter (ADC hereinafter) makes measurements by means of a 12 or 14 bit digitizer. This level of accuracy or precision can be varied to obtain the precision desired. A sign bit is normally included with this data.

From beat to beat, the same part of the signal is located. This is preferably the peak which is normally termed the R complex, and as noted before, location of such peaks in a series of heartbeats in effect measures the time interval from one beat to the next or the R-R interval. Other parts of the signal waveform can be detected, but it is generally easier to locate the R complex. As a generalization, the heartbeat length evidences a certain degree of randomness which is indicative of a healthy heart, or one that is not subject to lethal cardiac arrest. More particularly, there is a measure of randomness that can be described as a specified range which is indicative of a healthy heart while in contrast a prearrest condition does exist where there is a conspicuous absence of randomness. As a matter of background, the heart is a highly innervated structure and requires the integrity of its nerves for coronary artery occlusion to evoke ventricular fibrillation (Ebert et al., 1970). A descending neural pathway from the frontal cortex to the brainstem cardiovascular centers must also be intact for coronary artery occlusion to result in a lethal arrhythmogenesis (Skinner and Reed, 1981). Clearly then, the nervous system has an important role in lethal arrhythmogenesis, and its randomness in operation is indicative of a healthy/lethal condition.

Several cerebral mechanisms with cholinergic projections to the heart are responsible for controlling the heartbeat intervals (Kitney, 1987). Increased mental task-load in humans will block this cholinergic regulation (Mulder and Mulder, 1987). Such mental stress (e.g., mental arithmetic) will also reduce the threshold for electrophysiological induction of ventricular fibrillation in patients with a myocardial infarction (Tavazzi et al., 1986). In animals mild stresses (e.g., an unfamiliar environment or mild cutaneous stimulation) must be present for coronary artery occlusion to result in ventricular fibrillation (Skinner et al., 1975).

The frontal lobe is electrically reactive to stressors. Tonically evoked activity in this structure appears to provide the output over the frontocortical-brainstem pathway that must be present for the initiation of ventricular fibrillation in the acutely ischemic heart (Skinner and Reed, 1981; Skinner, 1985). This output appears to inhibit modulation of the heartbeat (Skinner, 1985).

In patients with a myocardial infarction, a reduced standard deviation of the R-R intervals predicts prospectively an increased incidence of mortality (Kleiger et al., 1987). A reduced baroreflex sensitivity to transiently induced high blood-pressure is also predictive of increased mortality in patients with a recent infarction (Schwartz et al., 1984). Thus the study of the heartbeat dynamics, which are controlled by specific cerebral mechanisms, may provide insight into the mechanism by which ventricular fibrillation is generated.

The observation of mathematical chaos in the heart may provide innovative ways for the cardiologist to monitor the sick, injured or aging heart and then provide the appropriate therapy. Under healthy conditions, the heartbeat is surprisingly erratic with spectra and phase space representations consistent with mathematical chaotic dynamics. Patients at increased risk of sudden cardiac death may show a loss of this physiological chaos, as well as abrupt changes resembling the bifurcations observed in the "logistic" function. Detection and quantification of such nonlinear dynamics in the heartbeat timing may provide an earlier early warning system for cardiac diseases and drug toxicities, as well as a new way to monitor the effects of aging (Furman et al., in press Goldberger et al., 1988, 1990, in press; Stambler et al., 1989).

Currently the analysis of electrocardiographic data from cardiac monitors is quite superficial, with attention paid primarily to the mean and standard deviation of heart rate, along with counts of various types of abnormal heartbeats. Yet, as illustrated in FIG. 1, two subjects may have virtually identical means and standard deviations of heart rate, but the patterns (i.e., dynamics) are different and so are the vulnerabilities to lethal arrhythmogenesis. It is the dynamics that carries the important diagnostic and prognostic messages enabling medical intervention.

Until recently, it was widely held that sudden cardiac death represented an abrupt change from the apparently periodic state of the normal heartbeat to one in which chaotic arrhythmias occur. Mathematically speaking, the word "chaos" means that when two points are placed next to each other but on different orbits of their attractor, they will get farther and farther away from each other as they travel in time over their separate trajectories through phase space (i.e., they will have divergent trajectories and therefore have at least one positive Lyapunov exponent). Work from Goldberger and associates, as well as others, has suggested that under normal conditions the heart has chaotic dynamics and that fatal disturbances of the cardiac rhythm are often preceded by a decrease in the degree of physiological chaos (Furman et al., in press; Goldberger et al., 1988, 1990, in press; Stambler et al., 1989). This represents a reversal in the usage of the term "chaos" when applied to the injured heart.

This reversal in perspective above chaos in the heart is illustrated in FIG. 2. It is the healthy heart that has a chaotic pattern in phase space. Goldberger and associates have reported two abnormal heart rate patterns, as shown in FIG. 3, in patients with severe left ventricular failure (a group at high risk of sudden death) and in patients who actually sustained a fatal or near fatal tachyarrhythmia while wearing a portable electrocardiographic monitor (Goldberger et al., 1988; 1990). One dynamic was termed the oscillatory pattern because it is characterized by low frequency (0.01-0.06 Hz) oscillations in sinus heart rate. The other dynamic they called the flat pattern because it is characterized by a marked reduction is beat-to-beat variability. These pathologic patterns are reminiscent of the reduction in heart rate variability and the low frequency oscillations ("sinusoidal" pattern) observed in the fetal distress syndrome. Similar dynamics occur prior to cocaine induced sudden death in ferrets (Stambler et al., 1989). A reduction in heart rate variability and its chaotic dynamics also occurs in aging (Furman et al., in press).

Based on finding such as these, cardiologists are now pursuing ways of identifying nonlinear transitions such as bifurcation behavior and the loss of physiological chaos that may precede fatal cardiac disturbances. A variety of approaches are being followed, including spectral estimates, measurement of Lyapunov exponents and calculation of the correlation dimension. Important mathematical and technical issues, such as the problem of biological stationarity and the accuracy of computerized algorithms, need to be resolved before such measurements can be reliably applied to biological data sets and computed "on-line" by physiological monitors. The on-line monitoring process will be described to include the initial step of setting up the process by loading a set of dynamic data. Once loaded, and dependent on CPU speed, calculations relating to a single heartbeat can be run as soon as that beat has been completed, and the data provided is almost instantaneous. Those in the field hope that within the coming decade assessment of such nonlinear indices will provide cardiologists with important new techniques for identifying high risk patients at an earlier stage in the development of their disorder. These new indices may also enable more appropriate observation of the pathology, as they are linked more directly to the mechanism of arrhythmogenesis and not merely attached to a correlate, such as heart rate variability, that may or may not be appropriate. Such innovations are expected to allow detection prior to the manifestation of the life threatening and fatal arrhythmias and to be more effective in monitoring clinical treatments. An example of one device is described in the brochure from Cherne Medical. This device and method claims 75% correspondence between the chaotic analysis of one heartbeat recorded simultaneously from many electrodes and the degree of coronary artery occlusion as determined by coronary angiography in a cardiac catheter laboratory in a medical center hospital. That technology is clearly divergent from that to be described below in which the Point-$D_2$ method is used to evaluate vulnerability to lethal arrhythmias.

Ideker and colleagues (Chen P-S et al., 1986) are taking advantage of recent advances in electronic and computer technology to investigate the mechanisms by which the lethal cardiac arrhythmia is initiated. They record simultaneously from 138 or more electrodes placed on and in the hearts of animals and of patients undergoing heart surgery to track the spread of the wavefronts of cardiac excitation during fibrillation (Ideker et al., 1987). They also developed techniques to record potentials created throughout the heart by large electrical stimuli, such as defibrillation shocks. These investigators are using such instrumentation to investigate the mechanisms by which large electrical stimuli delivered during the recovery portion of the cardiac cycle, called the vulnerable period, can initiate ventricular fibrillation.

Before the advent of computer-assisted cardiac mapping techniques, the principal cause for the electrical initiation of fibrillation during the vulnerable period was thought to be heterogeneities in the electrophysiological characteristics of the myocardial cells (Han and Moe, 1964). As stated by the non-uniform dispersion of refractoriness hypothesis, a large electrical stimulus given during the vulnerable period will conduct away slowly from the site of stimulation because the cells are not yet fully recovered. If the refractory periods of the individual cells are dispersed nonuniformly, then the activation arising at the site of electrical stimulation will fail to propagate into regions that are still refractory, while it will propagate into neighboring regions that are more recovered. If a more refractory region has sufficiently recovered during the time the activation front propagates through any adjacent less refractory region, then this activation front can enter the distal portion of the more refractory region and propagate back towards the site of electrical stimulation. If the tissue first excited by the electrical stimulus has had time to recover, it can then be re-excited by the propagating activation front, producing a so-called reentrant circuit. If this reentrant circuit persists and begets daughter reentrant circuit, then ventricular fibrillation is thought to be produced.

The present invention applies an analysis to the R-R interval measurements. Thus, these measurements are analyzed to locate a subtle representation of the randomness which is present in the data. This has several benefits. It is able to arrive at a useful indicator with a smaller set of data. By contrast, perhaps 5000-50,000 or more heartbeats were required heretofore, but the present approach uses as few as only 1000 heartbeats, and it is thought to be possible to make this analysis wherein N is in the range of about 2500 or less, the lower limit not yet being determined. Moreover, it is able to accomplish that analysis in relatively quick order. It can, in fact, provide an indication for an individual as opposed to merely grouping the individual in broad categories (i.e., healthy versus unhealthy). The output of the present procedure is a specific indication of vulnerability to lethal myocardial infarction (MI hereinafter). That indication can be expressed as a simple number with an indication of the statistical standard deviation (SD hereinafter) attached. For instance, a healthy heart is indicated by a measure of 2.10 while an unhealthy heart is indicated by an evaluation of 1.0. In very general terms, chaos analysis, as taught herein, does not require stationarity of the biological generator (i.e., the human nervous system operating the heart in timed fashion) and relies on the lack of stationarities and makes measurements which are then used in an algorithm for determining the correlation dimension ($D_2$ hereinafter). This involves the sequential interaction of a routine for determining the scaling region over which the point scaling dimension is evaluated and another routine which determines whether or not the slope of the scaling region converges to a horizontal asymptote as the embedding dimension increases in value. The height of this asymptote is $D_2$. One of the benefits of this is the total number of data is so much smaller. Another advantage of the present apparatus is that the data which is obtained by the system can be analyzed almost in real time. It can operate readily with a patient whose heart rate is 60–90 BPM and thereby provide analysis of this data at rates ranging from 50% to 100% of the heart rate depending on the speed of the computer used. Utilizing a personal computer based on the 386 Intel brand processor installed into a machine with adequate memory and capable of operations at perhaps 16 MHz up to perhaps 30 MHz, substantially real time operations can be achieved. Moreover, this can be accomplished without an excess memory capacity. This is accomplished with a conventional set of electrodes installed in a conventional pattern for measuring the heart beat. Many other advantages of the present apparatus will become apparent on a review of the below included specification in conjunction with the drawings which are attached.

INTRODUCTION FOR THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIGS. 1A and 1B compare two heart rate time series with nearly identical means and variances yet one show normal, chaotic appearing fluctuations which the other is from a patient with severe heart disease and shows large amplitude, relatively periodic oscillations;

FIGS. 2A–2C show normal conditions where the heart beat time series fluctuates considerably on a beat-to-beat basis with a broad power spectrum with an amplitude inversely proportional to frequency;

FIGS. 4A–4D show initiation of reentry and ventricular fibrillation following the interaction of orthogonal gradients of myocardial refratoriness and potential field;

Figure 12:
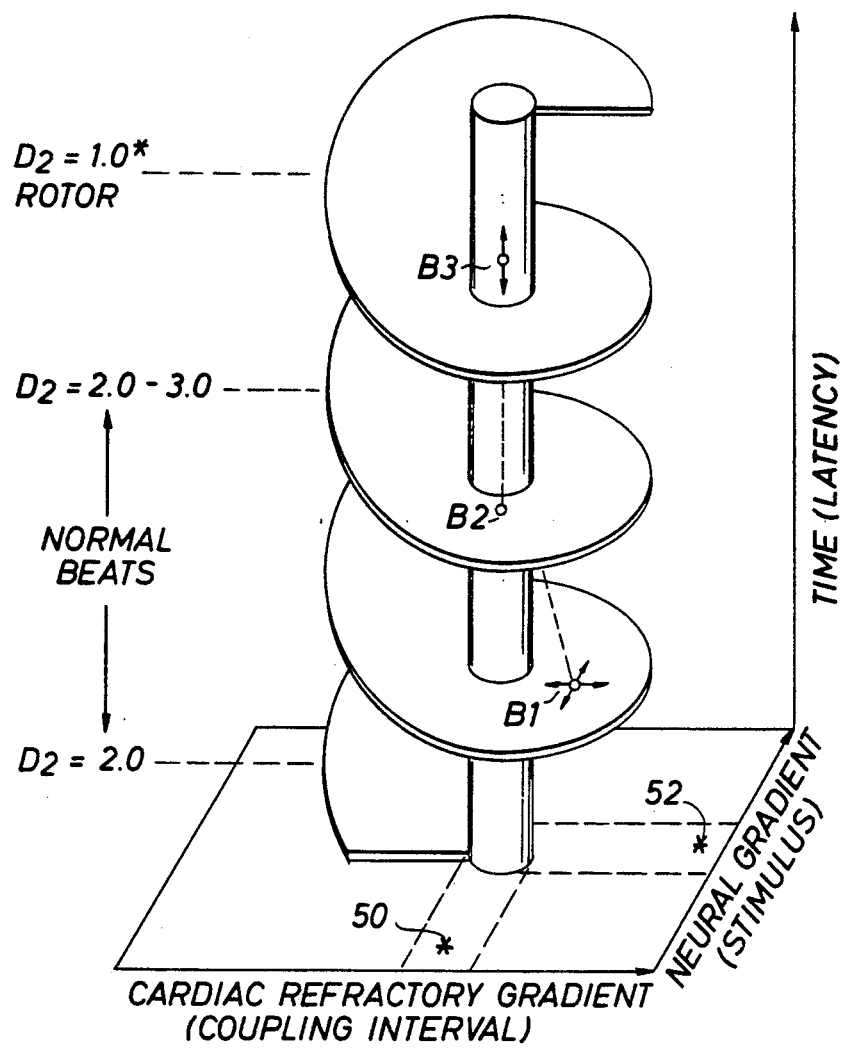
Figure 15:
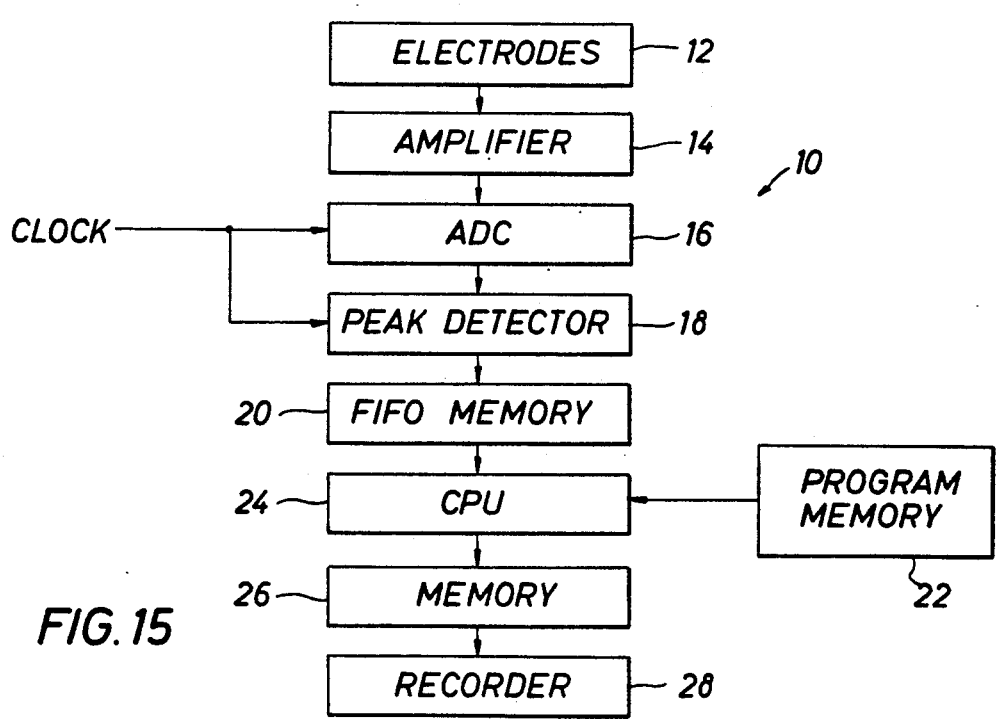
Figure 14A:
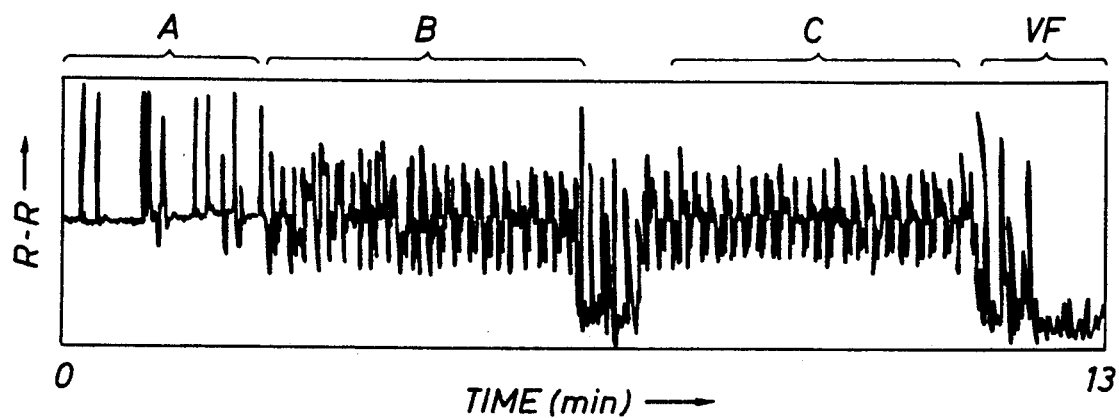
Figure 14B:
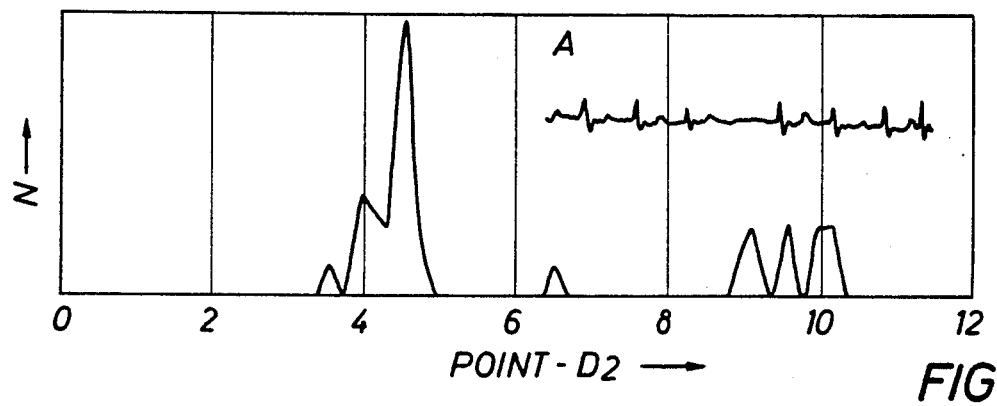
Figure 14C:
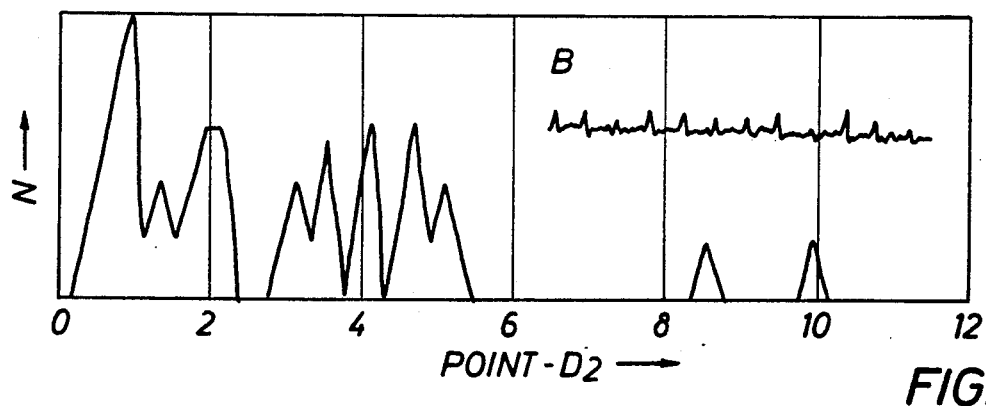
Figure 14D:
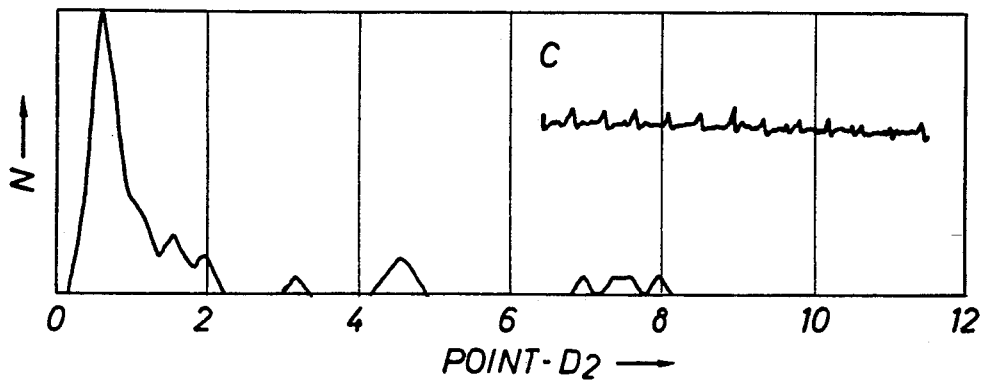
Figure 16A:
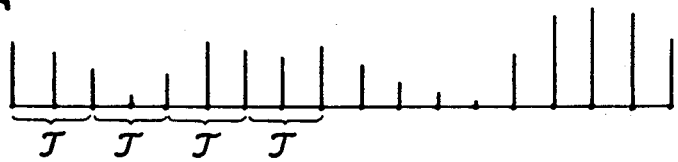
Figure 16B:
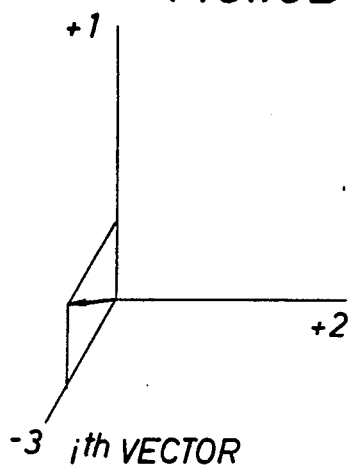
Figure 16C:
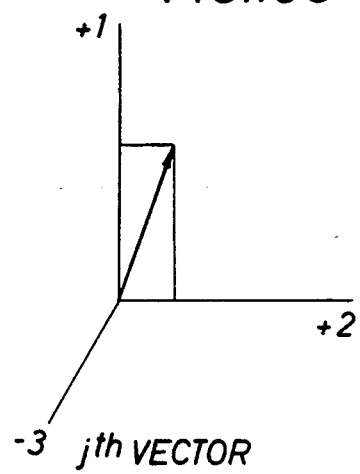
Figure 16D:
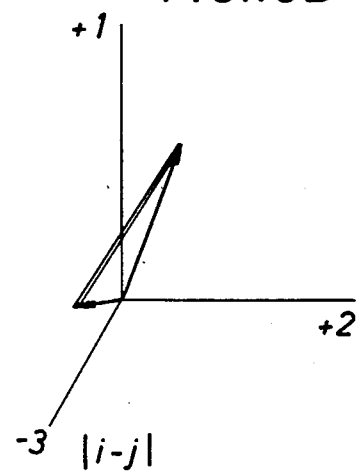
Figure 16E:
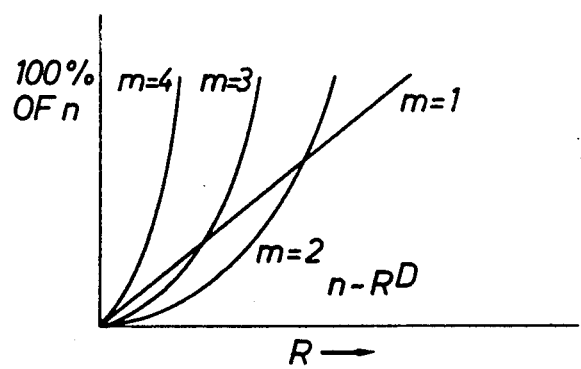
Figure 16F:
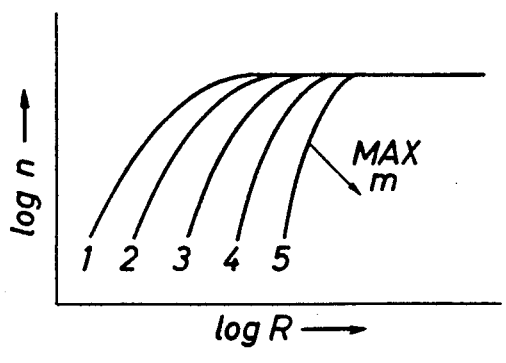
Figure 16G:
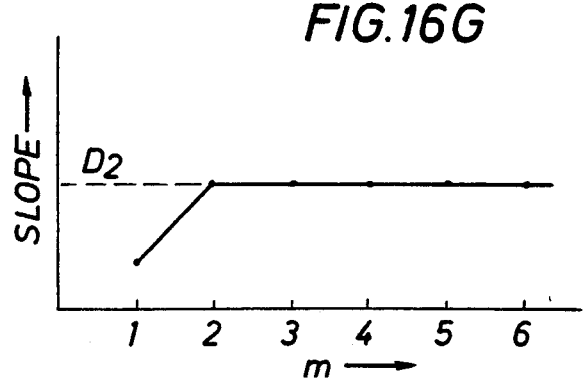
Figure 17A:
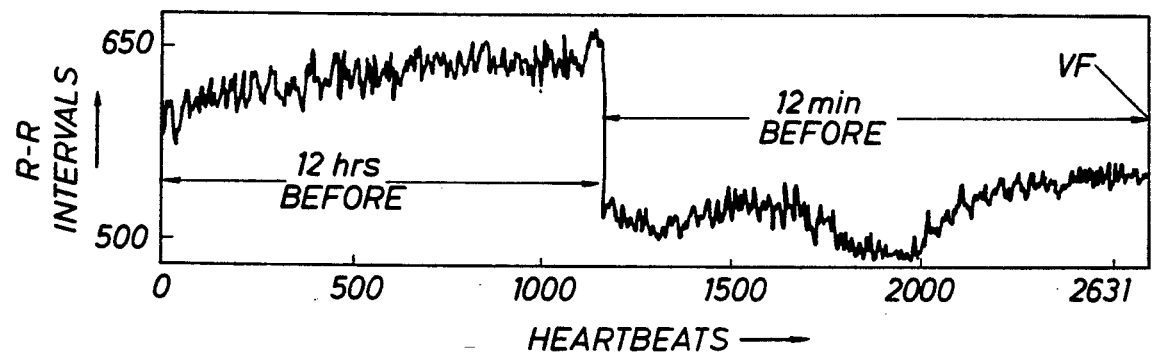
Figure 17B:
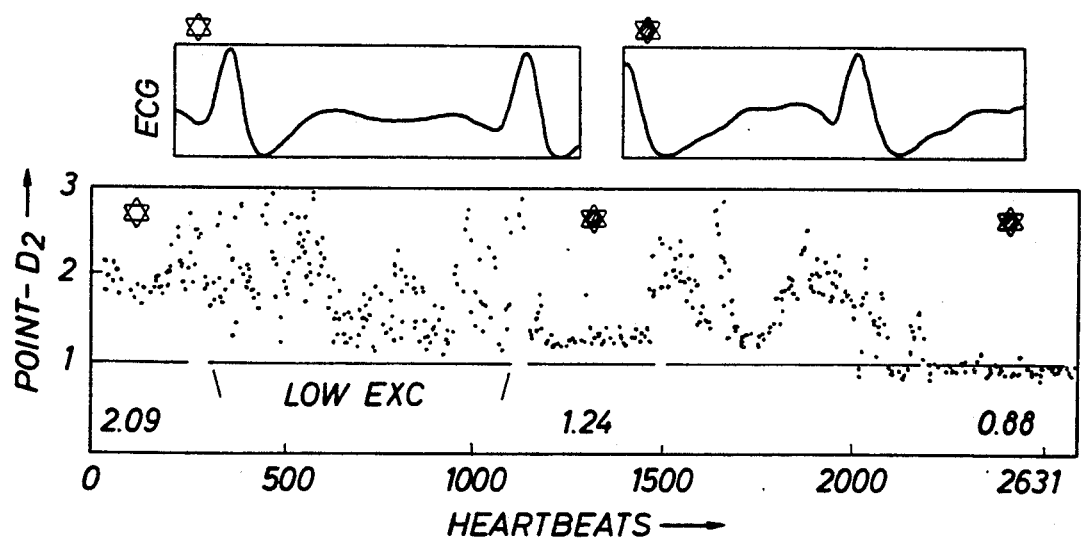

FIGS. 11A–E show changes in the distribution of the Point-$D_2$ values of the heartbeat evoked by acute myocardial ischemia (i.e., 100% occlusion of the left anterior descending coronary artery) in the conscious pig where the control R-R intervals (C) were recorded during the same session as those during 100% occlusion of the left anterior descending coronary artery;

FIG. 12 is a theoretical relationship showing the correlation dimension of the heartbeat to the Winfree model of excitable media applied to the heart;

FIGS. 13A-C are an electrocardiogram of a patient who died while wearing a Holter monitor;

FIGS. 14A-D are Point-$D_2$ distributions of heartbeats of data shown in FIGS. 13A-C where the upper curve shows R-R intervals with subepochs specified by A, B, and C shown in FIGS. 14B, 14C and 14D;

FIG. 15 is a schematic block diagram of a system in accordance with the teachings of the present disclosure;

FIGS. 16A-G show one explanation of chaotic analysis in accordance with the teachings of the present disclosure; and FIGS. 17A-17B are a further detailed analysis of data from a person who suffered a fatal ventricular fibrillation and includes data also shown in FIG. 13.

DETAILED DESCRIPTION OF THE PREFERRED EMBODIMENT

Attention is first directed to FIG. 15 of the drawings which shows a schematic block diagram of an apparatus for carrying out the method of the present disclosure. This will be described briefly to show how the data is generated. The apparatus is generally identified by the numeral 10 in FIG. 15. A set of electrodes 12 is illustrated. The electrodes are connected on a patient to be tested in accordance with this disclosure. The electrodes are affixed in a conventional spread or deployment on the body of the patient. There are specific locations set out for 3 electrode systems as well as systems involving a greater number of electrodes. In any case, the electrodes are attached in the specified locations, and data is recorded to obtain approximately 2500 or fewer heart beats. This is represented by N and is the set of data. Presumably, the patient has a heart beat which is perhaps as low as about 50 up to about 100. To obtain 1000 heart beats, it takes approximately 12 minutes or more in most patients. Ideally, the patient is at rest. The signals from the electrodes 12 are provided to suitable signal amplifiers at 14 and are then input to an analog to digital converter or ADC 16. In accordance with timed operations of the ADC as directed by a clock, digitizing occurs. The heart beat signal is digitized at some suitable rate such as 128, or even better at 256 times per second. It is also acceptable to provide more rapid digitizing, and as noted earlier, the digitizing occurs with an accuracy achieved by typical 12 or 14 bit digitizers. The output is provided to a peak detector 18. That is connected to memory 20, and in particular, a memory which operates on a FIFO basis. The FIFO memory is provided with timed measurements from the peak detector. As a generalization, the memory holds the measurements in sequence discarding the oldest data when storing the newest data. This can also be done with a ring buffer of N length. Each data entry newly placed in memory is used in a chaotic calculation to be described. It should be noted that the peak detector is capable of detecting the peak amplitude, but that is less important than the timing of the peak. The peak of the signal is measured and hence, the present disclosure speaks of measuring the R-R interval which is the time spacing from peak-to-peak or from beat-to-beat. These are measured, and they show a variation which will be analyzed in accordance with the teachings of this disclosure. The FIFO or ring memory need only contain N entries; that is, if N is set at 1000, there is no need to store 2000 entries. Accordingly, it operates on a first in, first out or FIFO basis. The oldest data in the memory 20 is dumped when the newest entry is input to it. This will provide a set of N data which is useful in making the analysis described below. The memory 20 is to be distinguished from a program memory 22 which stores the program which to be described. That N data is provided to the CPU 24. That makes the data analysis which in turn forms a suitable output which is provided in an output memory 26. Optionally, the data can either be stored or alternately, it can be provided to some kind of recording device 28.

Figure 3A:
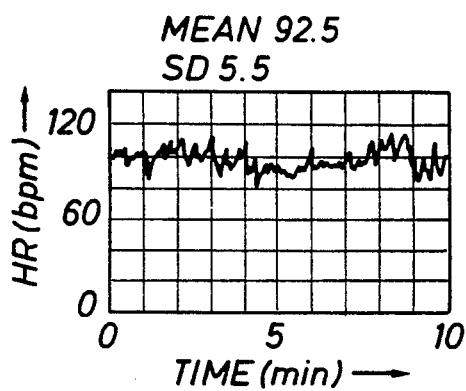
FIGS. 3A, 3C and 3E show the normal three different heart rate time series where
Figure 3B:
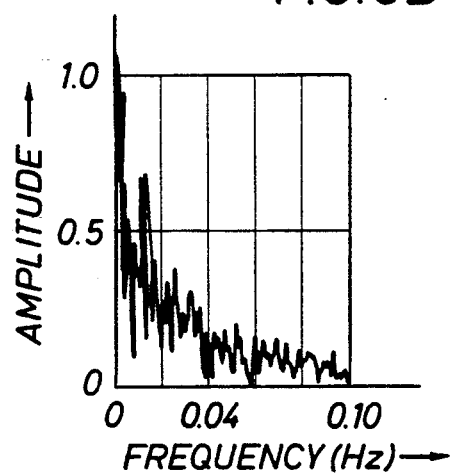
FIG. 3B shows erratic fluctuations and is represented by a broad 1/f spectrum while patients at high risk of sudden cardiac death may exhibit either (FIG. 3D) relatively slow oscillations or (FIG. 3F) showing a marked overall reduction in variability.
Figure 3C:
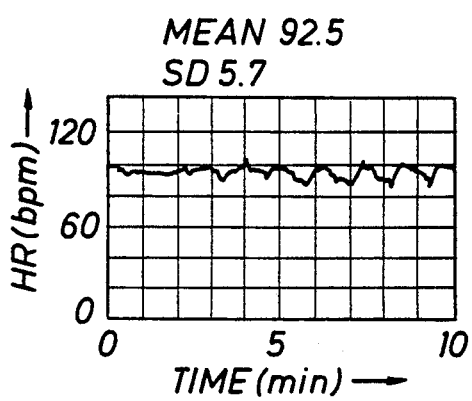
Figure 3D:
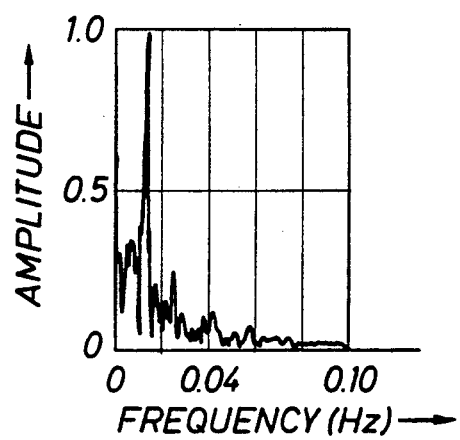
Figure 3E:
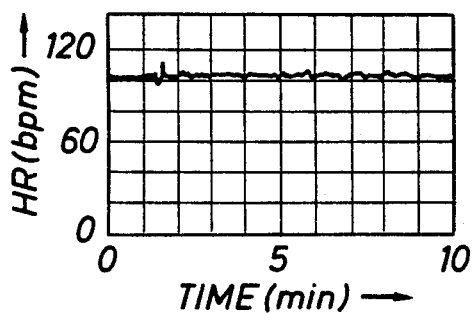
Figure 3F:
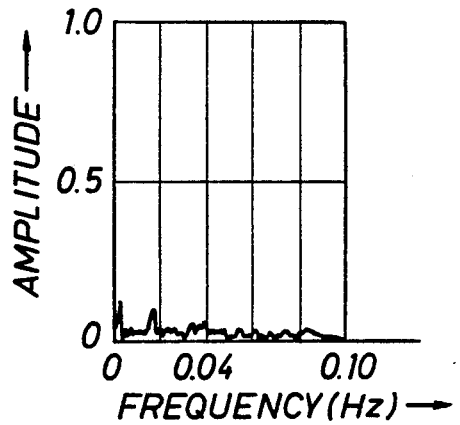

Attention is next directed to FIGS. 1A and 1B of the drawings. The two graphs shows two separate heart rate time series which have nearly identical means and variances as indicated by the SD of 5.5 and 5.7. The graphs in FIG. 1A (for a normal or healthy beat) is more chaotic in appearance. By contrast, the graph in FIG. 1B was obtained from a patient with severe heart disease and shows large amplitude, relatively periodic oscillations in the heart rate. FIGS. 2A, 2B and 2C incorporate three specific representations from a heart beat time series (FIG. 2A) which shows fluctuations on a beat-to-beat basis. The phase space delay map of FIG. 2C shows a trajectory which is consistent with a chaotic attractor as will be detailed hereinafter. Note also the substantial component in the frequency spectrum at the very lowest end of FIG. 2B. FIGS. 3A to 3F represents three different heart rate time series wherein one is normal and yet evidences erratic fluctuations. The normal heart rate of FIGS. 3A and 3B has a broad inverse frequency spectrum. By contrast, high risk patients typically show heart rates as evidenced at 3C and 3D which is evidenced by either relative oscillations or a notable overall reduction in variability at, see FIGS. 3E and 3F. Again, reliance on the heart rate average and standard deviation is simply not sufficient because FIGS. 3A and 3C show the same mean and standard deviation.

Figure 4A:
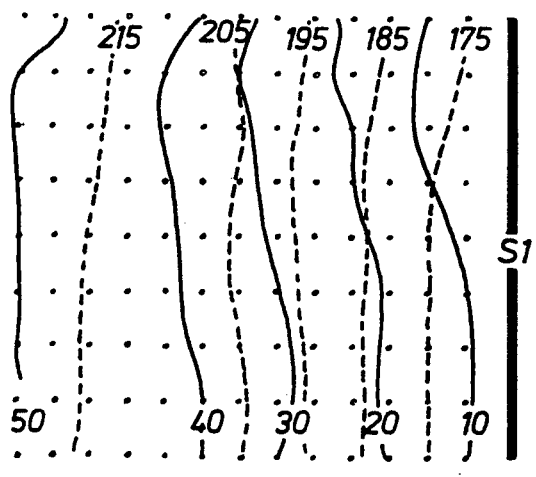
Figure 4B:
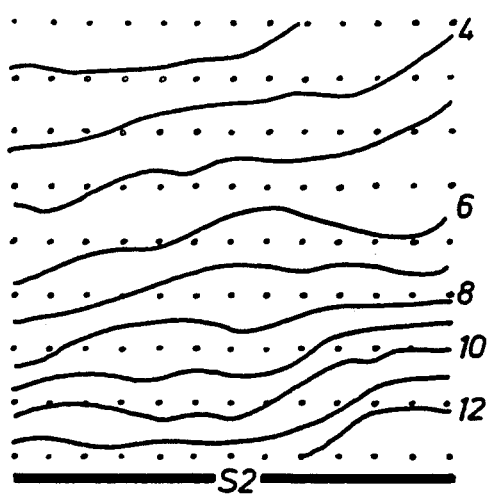

FIG. 4 of the drawings shows mapped data across the heart surface as for example in animal tests such as a dog. At FIG. 4A, there is a distribution of activation times and refractoriness following the last of 10 beats at a regular pace, located at S4 in FIG. 4A. Wavefronts are identified in the pattern. There are 117 recording electrode locations arranged in a 9×13 grid pattern on the epicardial surface which is a surface area of approximately 3 cm by 3 cm on the dog heart. Regularity in the spacing was accomplished by installation of 8 epicardial stimulating wires to the right of the recording electrodes at S1. The solid lines in FIG. 4A are isochronal lines which represent the spread of the electrically initiated activation wavefront away from the S1 electrode FIG. 4A shows normally conducted wavefronts. The solid lines proceeding to the left from the S1 electrode are at spacings of approximately 10 milliseconds after stimulus. The recovery lines are dashed lines which were calculated at 32 sites evenly spaced across the approximate 3 cm by 3 cm array using localized cathode stimuli of about 2 milliamperes. It was observed that the refractory periods were similar at all electrode sites and were approximately 166+/−3 milliseconds. This clearly indicates that there is a minimal number of inhomogeneities in the system. Because of the near uniform nature of the heart muscle in this region, uniform and parallel isorefractory lines can be created. However, and by contrast, FIG. 4B shows the potential (orthogonal voltage) gradient generated by a large premature shock as S2 which was of 3 milliseconds duration at 150 volts from a mesh electrode measuring 4.5 cm by 1 cm positioned immediately adjacent to the recording electrode array. This created isogradient lines perpendicular to the isorefractory lines. The isogradient lines are spaced at 1 volt/cm. The S2 gradient is approximately 4 volts/cm.

Figure 4C:
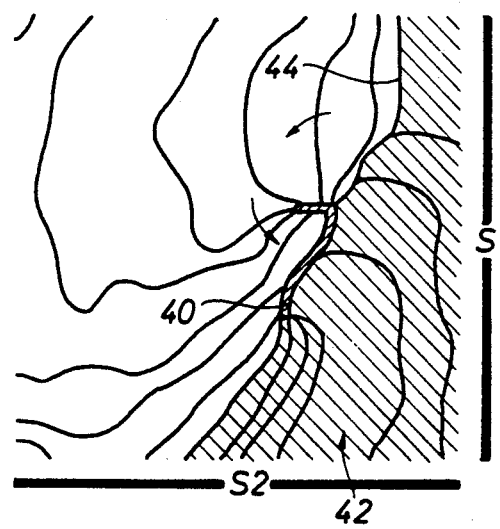

The recovery time is a key factor in FIG. 4C. More specifically, FIG. 4C represents the beginning of ventricular fibrillation (VF hereinafter). The activation times are measured from the start of the S2 stimulus which is by definition premature. The isochromes are shown at 10 milliseconds intervals. Initial conduction appeared as an activation front which terminates at the center of FIG. 4C and which extends some distance from the S2 electrode. The isochrome spread toward areas of later refractoriness produced by the S1 stimulus and formed a rotator of reentry around an arc of temporary conduction blockage which is the hatched line 40 in FIG. 4C. The larger shaded area 42 represents the regions recovering from the S1 stimulus that, without the critical timing, would be directly excited by the S2 stimulus. Clockwise reentry was generated as evidence by the arrows in FIG. 4C. An initial site of rotator formation was at a potential gradient of approximately 5 volts/cm and at a point where the heart tissue was just emerging from its refractory period from the last regular S1 stimulus at the time the large S2 stimulus was given. The solid line 44 represents the frame line transition between this particular activation map and a similar map for the next cycle of reentry should one occur.

Figure 7:
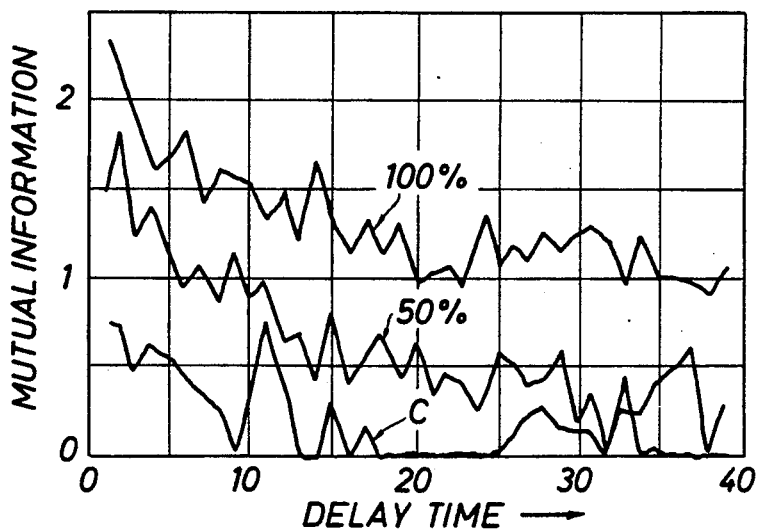
FIG. 7 shows mutual information content of R-LR intervals from a healthy control (bottom curve) following sustained 50% occlusion of the left anterior descending coronary artery (middle curve) and complete occlusion of the left anterior descending coronary artery (top)
Figure 5:
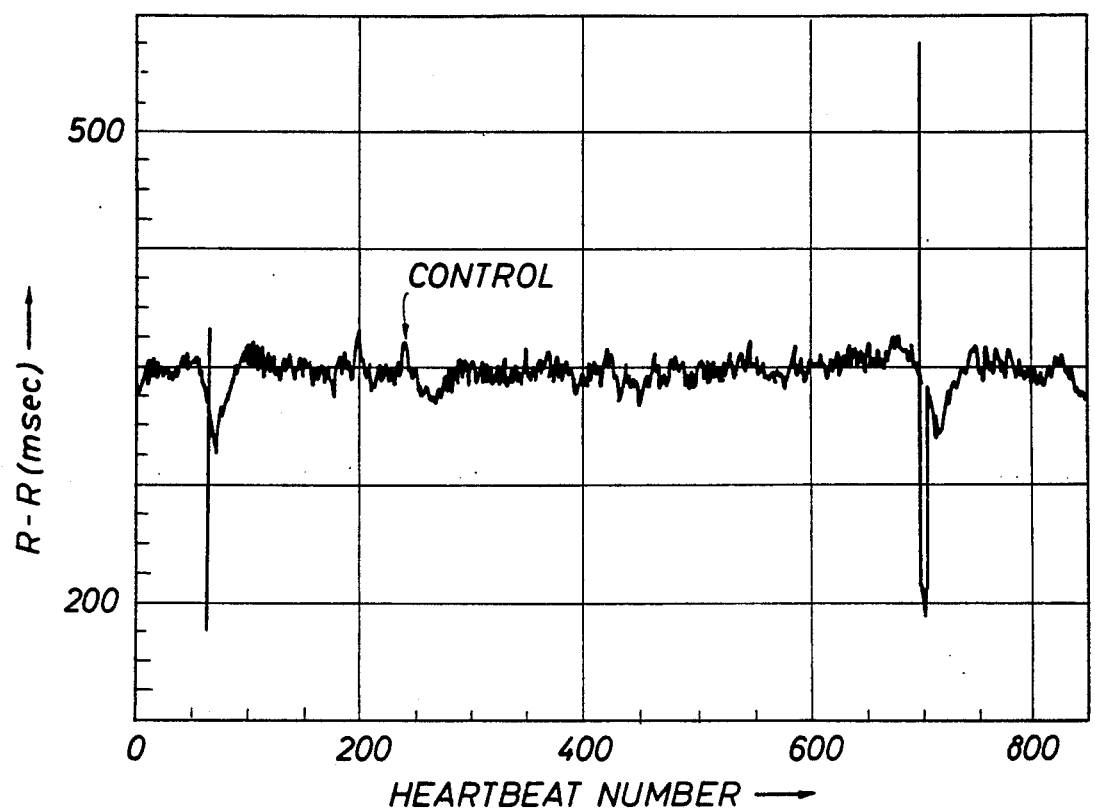
FIG. 5 shows approximately 8 minutes of R-R intervals recorded from a standard ECG lead attached to a conscious and alert pig.
Figure 6:
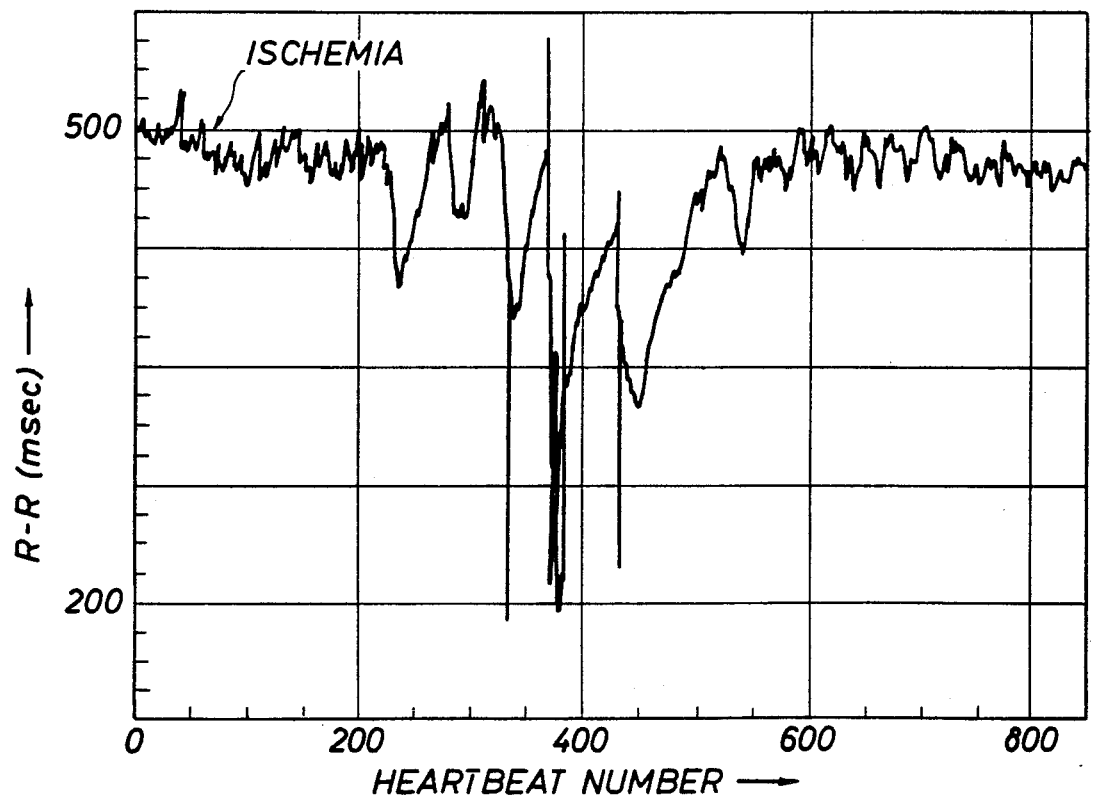
FIG. 6 shows approximately 8 minutes of R-R intervals recorded from the standard ECG lead of the same pig immediately following 100% occlusion of the left anterior descending coronary artery.
Figure 8:
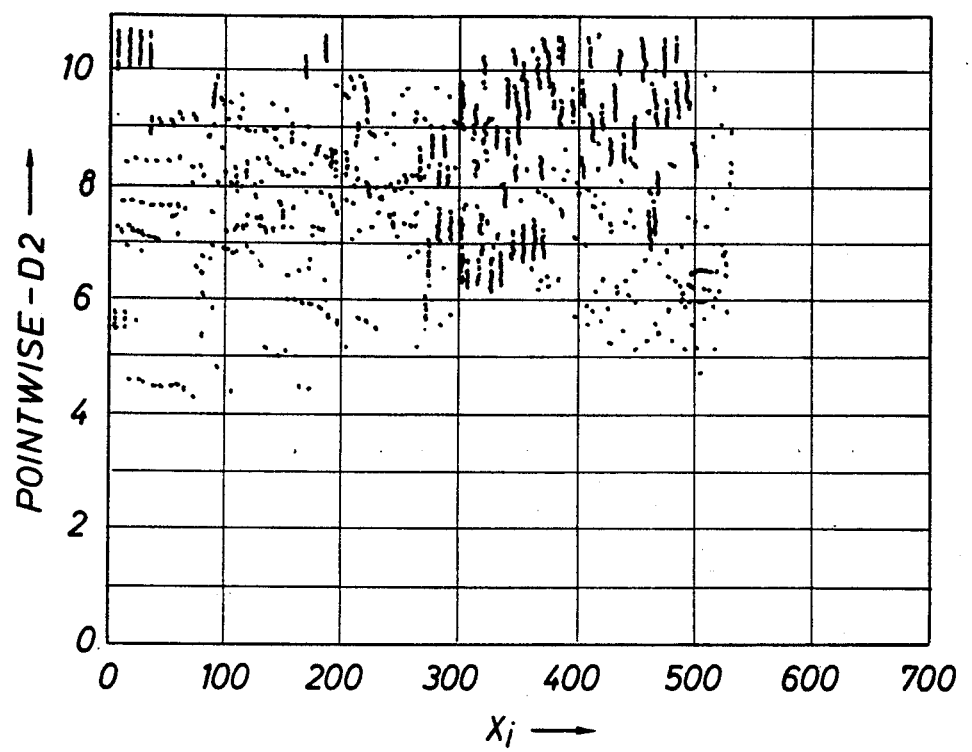
FIG. 8 shows a time series of the Pointwise correlation dimension values for the heartbeats shown in FIG. 5.
Figure 9:
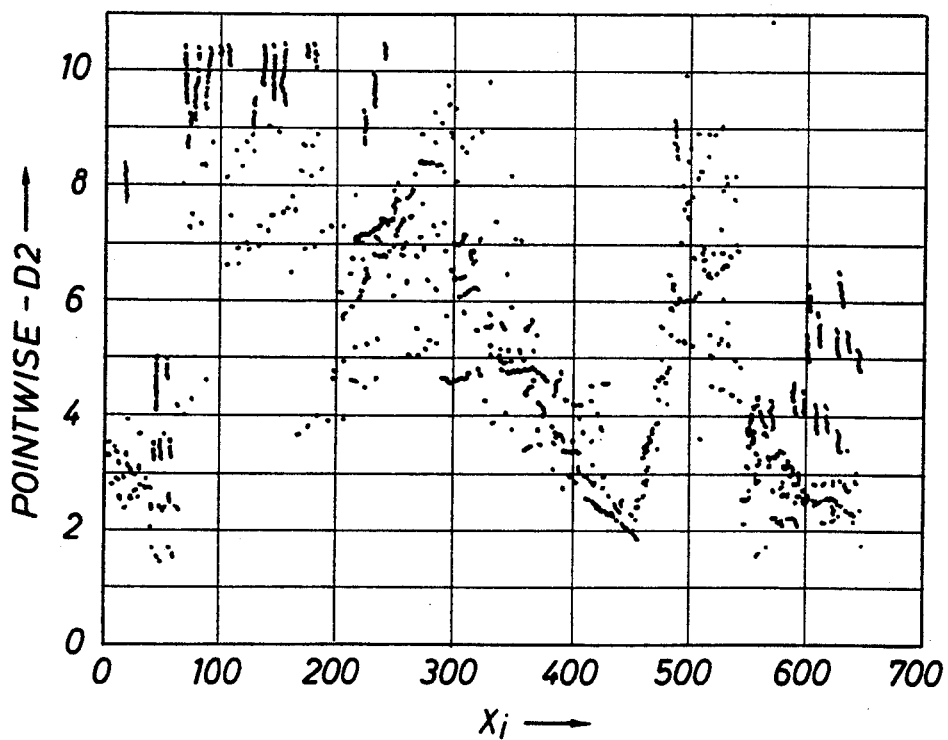
FIG. 9 is similar to FIG. 8 and shows the same for the data of FIG. 6.
Figure 10A:
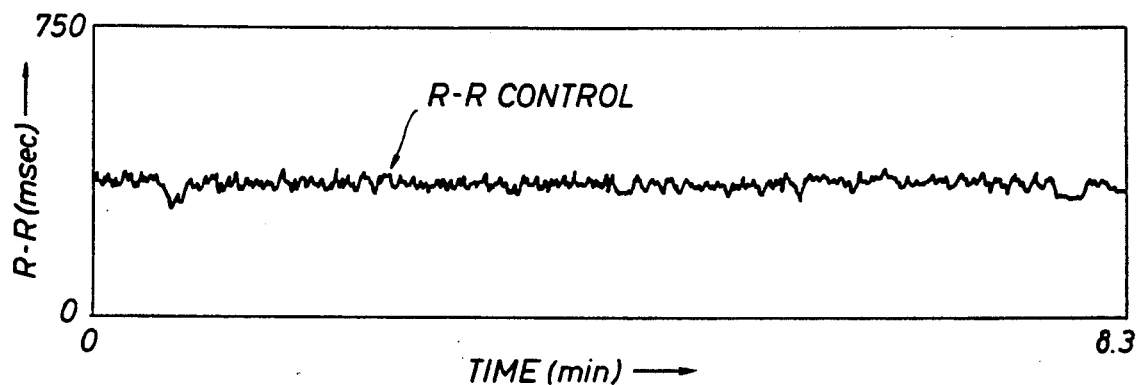
FIGS. 10A, 10B and 10C show changes in the distribution of the Point-$D_2$ values of the heartbeat evoked by psychological stress from a quiescent control period and during psychological stress period in FIG. 10B and the changes in point-$D_2$ over 12 minutes compared to 8.3 minutes.
Figure 10B:
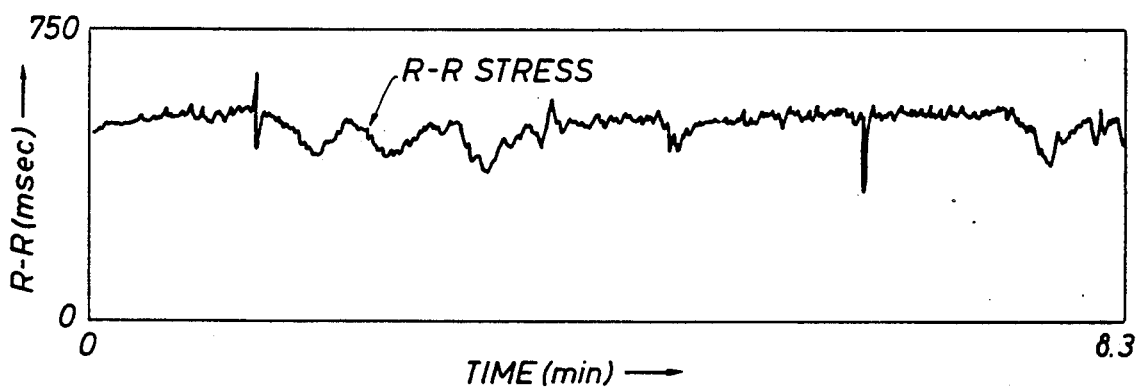
Figure 10C:
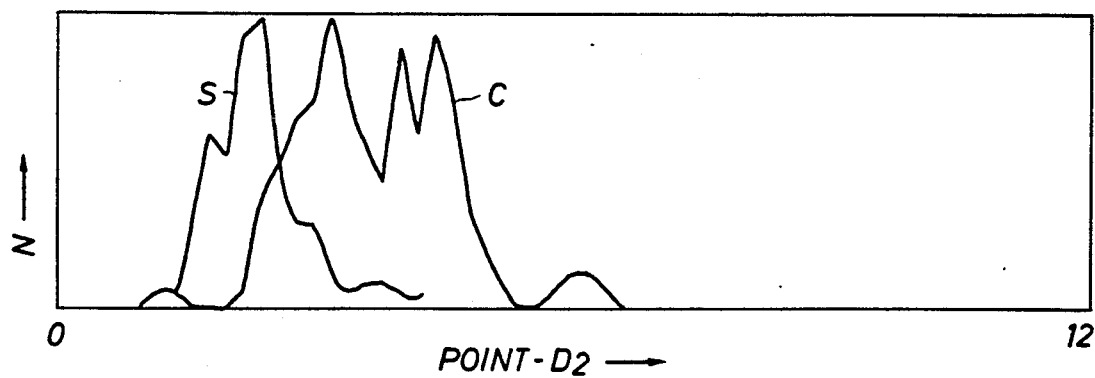

Consider FIGS. 5 and 6 jointly. They both represent the measured spacing from peak-to-peak of approximately 800 heart beats as reflected in the ordinate of FIGS. 5 and 6. They are both derived from a conscious pig. In FIG. 5, the animal was alert and awake. In FIG. 6, the data was obtained immediately following 100% occlusion of the left anterior descending coronary artery. Thus, FIG. 5 represents the control data, and FIG. 6 is the ischemic data. Amplifying on that, FIGS. 8 and 9 are similar in construction, but clearly point out the benefits of the present approach. Briefly, FIG. 8 shows the determinations of the pointwise-$D_2$ values for the heart beat data from FIG. 5 or the control data. FIG. 9 shows the same data derived from FIG. 7 where the animal suffered 100% occlusion as mentioned. FIGS. 8 and 9 considered jointly are derived in the same fashion. As will be detailed hereinafter, a time delay for $\tau$ is 9. As will be explained, 669 vector data points were obtained for an embedding dimension of 20, and the first 650 vectors were selected as reference vectors to calculate the vector difference sets for the 20th embedding dimension. Certain points were rejected from this $D_2$ set. If they were temporally close, they were rejected. The criteria for this rejection was determined where the absolute value of $i-j$ was equal to or less than 3 then the difference vector was disgarded. Comparison of FIGS. 8 and 9 shows a difference in chaos.

Figure 11A:
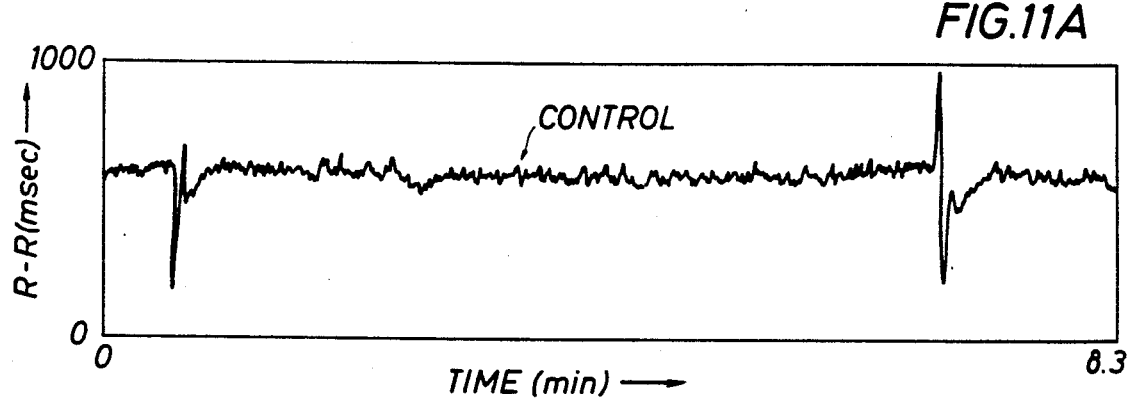
Figure 11B:
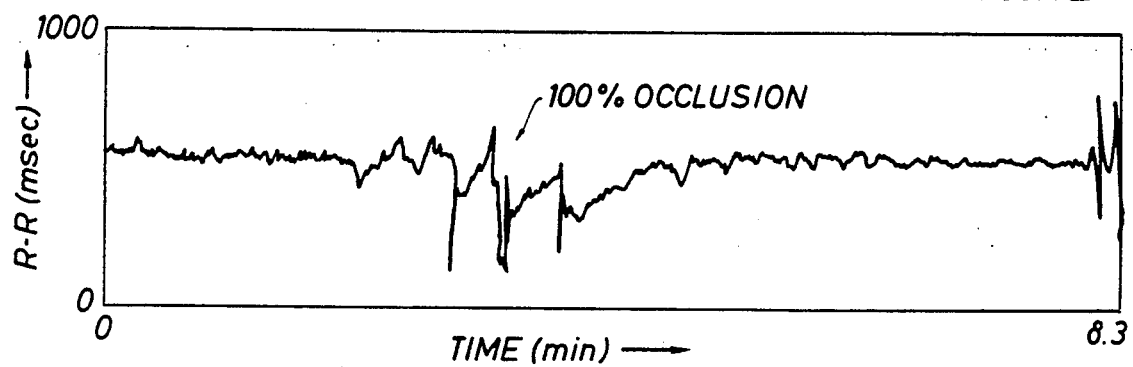
Figure 11C:
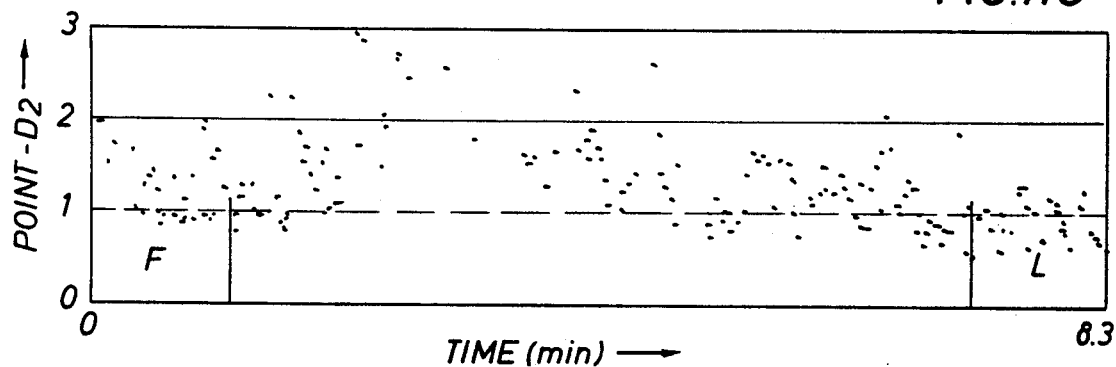
Figure 11D:
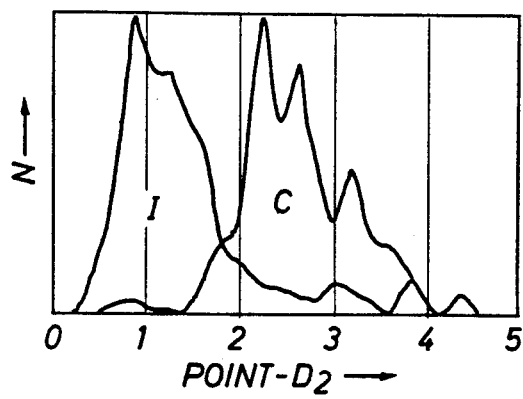
Figure 11E:
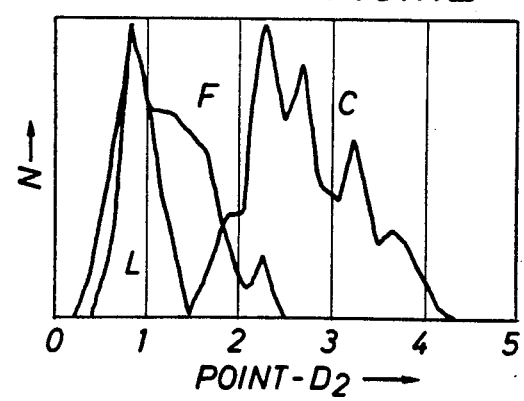

Going now to FIGS. 11A to 11E of the drawings, again using data from an animal having a coronary system similar to that of a human, the top data in FIG. 11A shows a measurement of the R-R spacing in milliseconds where the top curve is the control data. FIG. 11A control data was obtained during the same recording session as was the data in the next curve of FIG. 11B where the data is recorded over an interval involving 100% occlusion of the left anterior descending coronary artery. Contrast the R-R intervals in FIG. 11B showing the ischemic condition which extends from the occlusive event and ends just immediately before VF occurred. The Point-$D_2$ values for the control interval and the ischemic interval are shown in the curve in FIG. 11C. The notations I, N, and C indicate ischemic and control curves in FIG. 11D. In the of FIG. 11E curve, the data for the first minute and last minute of the ischemic interval are shown. One curve is indicated by F which represents the first minute and the curve L represents the last minute, and both are contrasted with the control curve at C in FIG. 11E.

Consider next the electrocardiogram of a patient who died which is illustrated in FIGS. 13A, 13B and 13C. This particular patient was wearing a Holter monitor system. The data at FIG. 13A shows the Holter system attached while FIG. 13B shows the patient 26 minutes before VF and FIG. 13C shows the patient 13 minutes before VF. This data is illustrated in FIG. 13 while FIGS. 14A to 14D depict that data. FIG. 14A is divided into separate epochs which are identified at the top where the R-R intervals are first illustrated. There, subepoch A shows a relatively normal set of data with occasional ectopic beats, see also FIG. 14B. The subepoch B shows a wide spectrum of $D_2$ values where some values extend through the 1.0 in FIG. 14D dimension value. This subepoch precedes an episode of ventricular tachycardia. The subepoch C shows reduced chaos where the Point-$D_2$ distribution is close 1.0 and immediately precedes a fatal VF episode of lethal arrhythmogenesis.

As can be seen from FIGS. 13 and 14, one of the benefits of the present procedure is made quite clear in the contrast where a predictive possibility arises in the subepoch C shown in FIGS. 14A and 14D, and the present apparatus is a system which provides such an indication.

Attention is now directed to FIG. 12 of the drawings which is a three dimensional model. The three dimensions are time in the vertical dimension with the neural gradient or stimulus deployed at right angles to the cardiac refractory gradient or coupling interval in the horizontal dimensions. This three dimensional representation is better understood by defining the coupling interval as the time related to the previous R-R interval at which a current is injected, referring to the isochronal data shown in FIG. 4. The stimulus is defined as the intensity of the injected current. The latency is defined as the latency to the next beat which either can be advanced or delayed by changing either the coupling interval or the stimulus intensity. The central stem of the image in FIG. 12 represents the unpredictable full cycle of latency that is either at the border of or above the point singularity in the toroidal plane of coupling interval versus stimulus shown in the illustration. Each full revolution of the flute is a full cycle of a latency that surrounds the point singularity. Connections between flutes produces a continuous time scale where the latencies of a series heart beats is specified by the intersection of the time trajectory with the respective flutes such as illustrated by the points B1, B2, and B3. It has been suggested that myocardial ischemia produces constraints on the degrees of freedom of the coupling interval and stimulus which are bracketed by the dotted lines or between the asterisks at 50 and 52. Thus, if the pairs of lines are closer, the bracketing effect is greater. That is to say, there is a reduction in the degrees of freedom. These variable constraints produce a rotator wave, and suggested values for the myocardium are about 191 milliseconds and 5 volts/cm respectively. The term rotator wave is different from that shown in the heart muscle in FIG. 4. Here, the rotator wave is a two dimensional surface having the form of a helix in space. The surface on the helix is only two dimensional even though that surface is deployed in three dimensional space. The central rod through the helix is only one dimensional, i.e., only a line. Normal heart beats as exemplified at B1 and B2 in FIG. 12 have correlation dimensions of $D_2$ of about $2.5 +/- 0.81$ in contrast with heart beats immediately prior to VF exemplified at B3 in FIG. 12 which have a $D_2$ of about $1.07 +/- 0.18$. Thus we see that the physiology of the heart, affecting the stimulus and coupling interval, determines whether two dimensional healthy system or a one dimensional unhealthy system occurs.

The system shown in FIG. 15 collects a data sequence of N data where each entry represents the measured elapsed time between beats. The chaotic analysis of this data will follow the description which is given by this simplified analogy for tutorial purposes. First of all, digitizing goes on during the heartbeat at a specified sampling rate. The sampling rate (mentioned above) creates a number of measurements which are recorded along with sign so that a procession of data points is available. A value of $\tau$ is selected, and that value can be 1, 2, 3, 4, etc. The $\tau$ is the delay to the zero crossing of the auto-correlation function. Next, in the procession of data points beginning with the value of $\tau$ as selected, a first vector is defined by obtaining values for that vector. This vector is in space including up to some selected value of maximum dimensions where the number of dimensions is represented by m and m is whole number integer which is one or greater. FIG. 16A therefore includes a set of measurements in digital form in time sequence, and the bracket in FIG. 16A represents the spacing or $\tau$. A set of points is selected (where m is a particular integer), and FIG. 16B shows the first vector that would be defined if m were three. The selected values define a three dimensional vector (recall that m is three) and those values are from the series in FIG. 16A, while the vector is represented in space at FIG. 16B. Repeating this as shown in FIG. 16C, a second vector is defined. For illustrative purposes here, both vectors are shown for m=3 because it is most readily represented in this tutorial. Conveniently defining the vector in FIG. 16B as the ith vector and the vector in FIG. 16C as the jth vector, FIG. 16D shows the difference between the two vectors. While FIG. 16D is the difference, only the absolute difference is needed so that the vector has been illustrated without an arrow to indicate that the absolute value is of interest and the direction of the vector is not important. The absolute lengths of the differences provide a set of data which are the absolute values obtained by making repeated subtractions across the whole set of data. Recall that FIG. 16A represents the data obtained from N heartbeats. Recall also that $\tau$, for this representative example, is two and the number of dimensions m is three; this defines a single vector from the set of measurements as illustrated in FIG. 16A. Vectors analogous to FIGS. 16B and 16C are thus obtained for the entire set of data, or to the last value of data. For every vector, the subtraction involves the first vector represented at FIG. 16B which is subtracted from the subsequent vectors determined in the fashion of FIG. 16D. This provides a set of difference values, used in the following steps. Since $\tau$ and m can vary, the foregoing should be repeated for different values but more will be noted regarding additional calculations later.

Assume for purposes of illustration that the difference values obtain by subtracting as described above is a set of values. A specified value for the minimum difference is established, and difference values less than this are discarded so that values above this value can then be used. FIG. 16E shows a plot for m of 1, 2, 3, etc. As will be observed in FIG. 16E, the values of m (1, 2, 3, ... to the maximum) provide specific curves. The ordinate extends to 100% of n. The curves extend up to the maximum value of 100%. FIG. 16F shows a log-log representation of values of n and R which show curves for the various values of m. Note that n is proportional to $R^D$. FIG. 16G shows the slope of the curves in FIG. 16F where the slope approaches a maximum value. Hence, the slope in the ordinate shows a ceiling for the values notwithstanding increase in m to a maximum value. FIG. 16F and 16G together thus show the value at which $D_2$ will not increase even when m increases. This convergent state includes the inflection point in the curve at FIG. 16G. Following this, it will then be seen that $D_2$ has been established. In the representative curves shown at FIGS. 16F and 16G, $D_2$ is two even though m increases without limit.

Because m must be varied for several values, the sequence described herein is iterated for values of m above one up to some specified maximum. The maximum for m is usually set to be at least twice as large as the expected $D_2$ result. Since m is varied, the set of data represented at FIG. 16A must be reprocessed for a different value of m. Accordingly, the sequence is repeated where m is set to 1, 2, 3, 4, ... up to a selective maximum. For each value of m, another curve is added at FIG. 16E, and the slope is ultimately derived by proceeding from FIG. 16E through FIG. 16F and then finally to FIG. 16G.

After the next heartbeat, the oldest data is discarded, and new data is input in sequence to the procession of data which is in memory. This then completely changes the values of the coordinates of the vector in FIG. 16C. Since it is used in a subtractive manner, it completely changes the values of the absolute difference after subtraction. The sequence of calculations is then repeated as illustrated in FIGS. 16E, 16F, and 16G. For the next heartbeat which is at N+2, all of the sequences are again repeated.

In summary, the procession sequence is repeated for each heartbeat, but it is also repeated within each heartbeat for multiple values of m where m is 1, 2, ... up to a maximum value. The foregoing suggests a rather massive set of calculations which, while numerous, can be readily executed with rapid dispatch with the representative computer mentioned in this disclosure. Calculations can be computed almost at real time depending on computer speed and the internal memory of the computer and its access time.

The indicator which is obtained by the slope intercept in FIG. 16G is indicative of dimensional analysis from the chaotic data, and that value is predictor useful for determination of the state of risk of the individual being test. Moreover, it can be provided substantially in real time as mentioned and will track the state of affairs immediately following entry of the last heartbeat and the data which is associated with it when presented in digitized form. As will be understood from the representative curves and particularly those relating to FIG. 13 where the patient providing that data died from VF, this kind of analysis will show a loss of chaos which is indicated where $D_2$ decreases. If $D_2$ decreases from a value of about 2.0 or greater and declines toward 1.0, this is quickly indicated as the measure of chaos decreases. The risk of the patient is thus directly indicated by this decline in the value $D_2$ as illustrated in FIG. 16G. Where $D_2$ is a value of 1, perhaps even less, the patient is at great risk. Moreover, this risk is evaluated dynamically.

Going now to FIGS. 17A and 17B of the drawings, this again represents data obtained from the patient who died from VF while on a Holter monitor system. This is the same data represented in FIG. 13 and analyzed in FIG. 14. This portion of the data from the Holter monitor was taken from that larger set of data and is 12 hours prior to VF and 12 minutes prior to VF. Thus, R—R intervals are shown in the curve of FIG. 17A. The intermediate curve represents the Point-$D_2$ data. At the first portion, the indication of 2.09 in FIG. 17B is relatively high showing a condition which is not susceptible to a fatal VF. However, there are reductions in the value to lower values, including in particular a cluster of data at a value of 1.24 which is ultimately decreased to 0.88 FIG. 17B. Sustained reductions to such low levels intrinsic in reduced chaos in the heart rate is precursor to VF and has been readily seen as a 100% predictor in animals nearing experimental MI. FIG. 17B further shows a relatively desirable ECG pattern which is associated with values of 2.09, and also includes at the right of FIG. 17B an ECG curve of a relatively unhealthy heart prior to fatal VF.

An important factor in the use of the present method in real time is the provision of an indication of $D_2$. Assume for purposes of illustration that the heart muscle is in some fashion damaged while a patient is in intensive care and being monitored in accordance with the teachings of the present disclosure. If the instantaneous calculation of $D_2$ drops from 2.00 or greater down to about 1.00 or some other value which is in a range indicating a precursor to MI or perhaps a fatal VF, an alarm condition is achieved and an alarm can be given by the monitoring system in accordance with the present method. Should the value of $D_2$ be that low for only a single beat or two, the alarm might not be sounded depending upon the number of beats creating a value of $D_2$ which is that low. Should however the $D_2$ value persist at a low level, then an alarm ought to be given calling for prompt medical intervention. By contrast, should an occasional value of $D_2$ determined for a single beat be low while other values are higher and indicative of good health, such indications would not necessarily indicate a persistent state at which an alarm condition existed. As a generalization, a drop in the instantaneous calculation of $D_2$ which persists is clearly is an alarm condition while a return to a higher value is not necessarily an alarming factor. Accordingly, the duration of $D_2$ data in the range of about 1.0 must be evaluated in light of other medical factors and the persistence of such low $D_2$ values. Again, referring the patient who provided the data in FIGS. 13 and 14 while on a Holter monitor and who subsequently died while on the monitor, there is a clear change in the data obtained twelve hours prior to VF compared with the data obtained twelve minutes prior to VF. Should a patient exhibit data similar to FIGS. 13 and 14 of this disclosure while in an intensive care unit, the patient would be typically provided with an IV solution at all times thus enabling emergency medical intervention whereby medication can be immediately administered to the bloodstream by injection and is otherwise subject to monitoring for other vital signs such as respiration, oxygen content in the blood, and so on. In summary regarding the indications of $D_2$, the data predicatively prompts medical intervention for prevention of MI.

The foregoing has described the present system installed for real time operation. Of course, sustaining real time performance is in part dependent on the processing speed of the particular CPU that is used. In real time operations, the device can be installed for monitoring critical conditions. For instance, for patients in an intensive care unit (ICU), they typically will be fitted with a set of electrodes in the chest area to monitor the heart beat, and that is typically transmitted by FM telemetry from the patient to a receiver customarily installed at the nearest nurse's station. The station is normally equipped with monitors which provide visual analog representations of the heart beat of all the patients in ICU. The present apparatus can be used at that locale for analyzing the patient's heart beat signal. In other words, specific connection to the patient is achieved by use of the electrodes already attached to the patient for the FM telemetry system. This permits the patient to be monitored with the present invention so that a precursor of VF can be obtained. Presently, the FM telemetry system is used merely to provide an indication of the onset of VF at which time immediate, drastic medical intervention is normally initiated. Through the real time analysis provided as described herein, medical intervention is triggered and an alarm condition in accordance with this disclosure will enable medical personnel to fully prevent, or at least reduce the impact of later VF. In addition to the real time operation as described, the present apparatus can be used as an analytical tool by reviewing data which was not captured in real time. For instance, a patient may wear a Holter monitor and the data can then be retrieved from the tape recording in the monitor and transferred for analysis by the present system. This approach contemplates testing after the fact. In that instance, real time operation may be of secondary value. The tape of data representing the heart beat of the patient can be analyzed and reviewed, perhaps functioning as diagnostic tools. In this particular approach, the output of the present system is primarily diagnostic in conjunction with other data regarding the patient.

While the foregoing is directed to the preferred embodiment, the scope thereof is determined by the claims which follow.

What is claimed is:

1. A method of analyzing heart beats to obtain an indication of heart conditions favorable to heart failure comprising the steps of:
   (a) measuring a series of N heart beats;
   (b) measuring in the N series the relative beat-to-beat timing and providing a series of such measurements; and
   (c) analyzing the beat-to-beat timing for chaos in the timing wherein the chaos is represented by an instantaneous value of dimension of the beat timing in a multidimensional representation of the chaos having values up to m dimensions where a healthy heart is represented by a higher dimensional value m and a lower value of m indicates a less healthy heart.

2. The method of claim 1 wherein the most recent heart beat interval added to the series of such measurements becomes the new reference point of the N series of measurements and the chaotic analysis is a function of the comparison between the most recent point and the previous N series of measurements.

3. The method of claim 2 wherein the N series is organized into vectors of m dimensions and a vector ($V_t$) is constructed in virtual space where the first coordinate $V_t(O)$ is the value of the $t^{th}$ point $X_t$, and $V_t(i)$ is the value of $X_{(t+i\tau)}$ and $\tau$ is the relative time delay.

4. The method of claim 3 wherein distances between the first vector and the other vectors are calculated, and accumulated into a cumulative frequency set where the number of distances less than r is measured for all values of r, from zero to a selected maximum separation distance for the vectors.

5. The method of claim 4 wherein a linear portion of this cumulative set, when logarithmically scaled, defines a scaling region.

6. The method of claim 2 including the first step of defining, for the set of measurements, a first vector in time, and second vector after the first vector; and
subtracting second and succeeding vectors from an earlier vector to obtain a set of vector differences wherein the differences are analyzed for an indication of relative heartbeat timing chaos.

7. The method of claim 1 wherein beat-to-beat timing is determined for a set of N beats, and the next occurring beat is timed while the oldest beat in the N series is discarded to update a stored file of beats in memory so that real time data input occurs followed by chaos analysis immediately following input of the most recent beat.

8. A method of testing heart conditions contributing to failure comprising the steps of:
(a) forming a series of timing measurements on successive heartbeats wherein the timing is for a series of N length in a serially arranged memory for the timing measurements;
(b) inputting the next occurring beat timing measurement and discarding the oldest beat timing measurement from the N series in memory;
(c) as each of a series of next occurring beat timing measurements is made, performing a new beat timing chaos analysis and providing an output in the form of a single value which indicates the measure of chaos;
(d) as subsequent beat timing measurements occur, obtaining additional timing chaos analysis values indicative of the measure of chaos; and
(e) forming an output record of values indicative of the measure of chaos as an indication of patient heart condition.

9. The method of claim 8 including the step of recording, after each newly measure beat timing input from a patient, the value measuring beat timing chaos and observing that value indicates changes in chaos and patient heart condition.

10. The method of claim 9 including the steps of:
(a) with the N series of beat timing measurements, and a selected value of relative timing $\tau$, defining a vector in m dimensional space with data from the series at $\tau$ spacing and selecting such data to serve as vector coordinates where the coordinates are, in sequence, 1, 2, 3, and up to m;
(b) varying m from 1 up to a whole number positive integer of selected maximum value;
(c) for a given m value, defining a first vector using the N series at the most recent entries;
(d) for the same m value, defining second and subsequent vectors until the N series is fully used to define vectors;
(e) forming a series of differences for the given m value by subtracting the first vector from all following vectors;
(f) forming a second series of differences for the next larger value of m by subtracting the first vector from all following vectors; and
(g) with the first, second and subsequent series of differences as m increases to the maximum value analyzing all series for values indicative of the measure of chaos.

11. A method for analyzing heart beat timing signals for the presence or absence of conditions indicative of impending heart malfunction comprising the steps of:
(a) converting a series of heart beat signals into serial time measurements;
(b) with the last occurring time measurement, performing a timing chaos analysis of the series of measurements to obtain a measurement of chaos;
(c) repeating the timing chaos analysis of the series of measurements to obtain a measurement of chaos with the next occurring time measurement;
(d) wherein the steps of determining a measurement of chaos represents chaos by determining an arithmatic value therefrom; and
(e) detecting in the chaos arithmatic value a value indicative of impending heart malfunction.

* * * * *